United States Patent [19]

Dwek et al.

[11] Patent Number: 4,659,659
[45] Date of Patent: Apr. 21, 1987

[54] DIAGNOSTIC METHOD FOR DISEASES HAVING AN ARTHRITIC COMPONENT

[75] Inventors: Raymond A. Dwek; Thomas W. Rademacher, both of Oxford, United Kingdom

[73] Assignee: Monsanto Company, St. Louis, Mo.

[21] Appl. No.: 693,075

[22] Filed: Jan. 22, 1985

[51] Int. Cl.$^4$ .................. C12Q 1/34; G01N 33/53; G01N 33/564
[52] U.S. Cl. ........................ 435/18; 436/94; 436/501; 436/506; 436/509; 436/827
[58] Field of Search ............... 435/14, 18; 436/501, 436/506, 827, 94, 95, 509

[56] References Cited

U.S. PATENT DOCUMENTS

| | | | |
|---|---|---|---|
| 3,088,875 | 5/1963 | Fisk | 167/84.5 |
| 4,189,466 | 2/1980 | Ainis et al. | 424/12 |
| 4,213,764 | 7/1980 | O'Connor | 23/230 B |
| 4,282,002 | 8/1981 | Prodell | 23/230 B |
| 4,420,461 | 12/1983 | Reckel et al. | 422/61 |

OTHER PUBLICATIONS

F. Mullinax et al, Arthritis & Rheumatism, 18, 417–418, 1975.
Kunkel and Tan, Adv. Immunol. 4, 351–395, (1964).
Pope et al., J. Immunol. 115, 365–373, (1975).
Hymes et al., J. Biol. Chem., 254, 3148–3151, (1979).
Duc Dodon et al., Immunol. 42, 401–407, (1981).
Rose & Friedman, Man. Clin. Immunol.; pp. 56–59, 178–185, 871–873, 2d ed., 1980.
Schur, New Engl. J. Med. 298 (3), 161–162, (1978).
Rademacher et al., Biochem. Soc. Trans. 11(2), 132–134, (1983).
Rademacher et al., Prog. Immunol. 5, 95–112, (1983).
Sox & Hood, Proc. Natl. Acad. Sci. U.S.A., 66(3), 975–982, (1970).
Spiegelberg et al., Biochem. 9(21), 4217–4223, (1970).
Sutton & Phillips, Biochem. Soc. Trans., 11, 130–132, (1983).
Montreuil, Ibid., 11, 134–136, (1983).
Takasaki et al., Methods. Enzymol. 83, 263–268, (1982).
Yamashita et al., Ibid., 83, 105–126, (1982).
Mizuochi et al, J. Immunol. 129(5), 2016–2020, (1982).
Glasgow et al., J. Biol. Chem. 252(23), 8615–8623, (1977).
Homans et al., FEBS Lett., 164(2), 231–235, (1983).
Thornburg et al., J. Biol. Chem., 255(14), 6820–6825, (1980).
Mullinax et al., Arth. & Rheumat. 19, 813, (1976).
Cahour et al., Biochim. Biophys. Acta 802, 188–196, (1984).
Day et al., J. Biol. Chem. 255(6), 2360–2365, (1980).

Primary Examiner—Sidney Marantz
Assistant Examiner—David A. Saunders
Attorney, Agent, or Firm—Scott J. Meyer; James W. Williams, Jr.

[57] ABSTRACT

A method is disclosed for the diagnosis of diseases having an arthritic component such as rheumatoid arthritis and osteoarthritis which comprises determining the deficiency of galactose in a sample of the patient's blood serum or plasma, or synovial fluid, or an Ig component or fragment thereof in comparison with the corresponding normal values of galactose.

1 Claim, 6 Drawing Figures

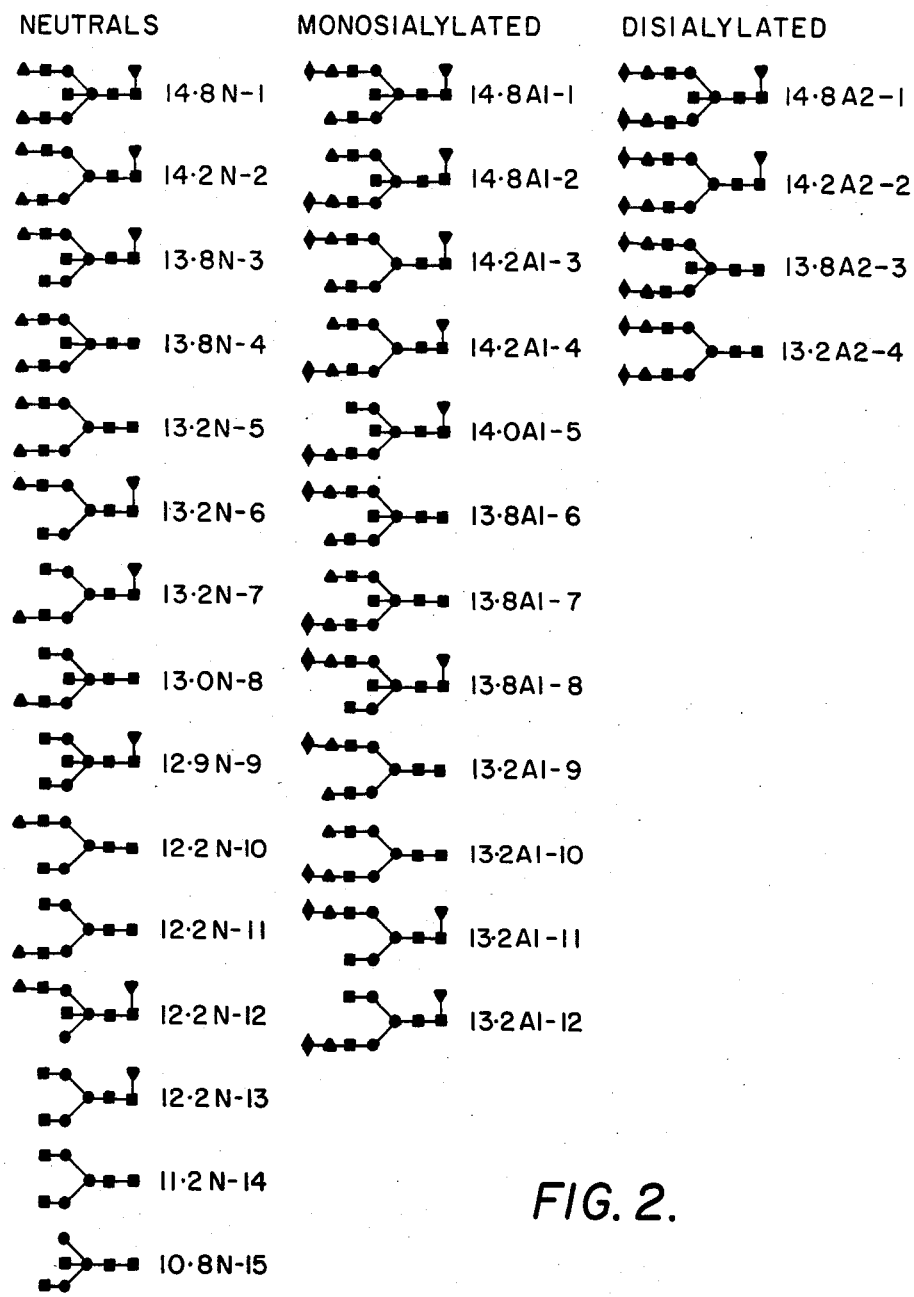
FIG. 2.
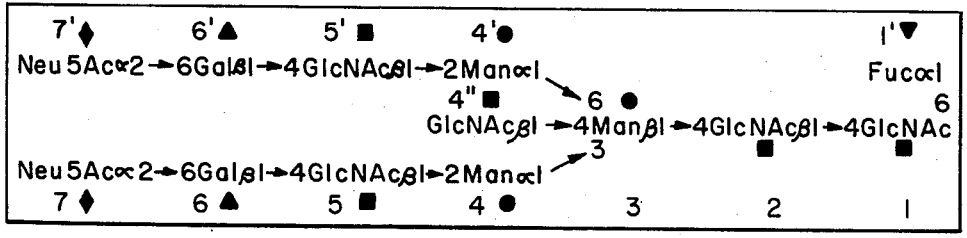

DIAGNOSTIC METHOD FOR DISEASES HAVING AN ARTHRITIC COMPONENT

BACKGROUND OF THE INVENTION

This invention relates to diagnostic methodology for diseases having an arthritic component, including rheumatoid arthritis, osteoarthritis and related conditions.

Rheumatoid arthritis is a widely prevalent, chronic systemic disease thought to have an auto-immune component. See, e.g., Kunkel and Tan, *Adv. Immunol.* 4, 351-395 (1964). Whether this immune response initiates, perpetuates, or is a consequence of the disease is at present not understood. Both humoral and cellular mechanisms have been proposed heretofore to be involved in the articular and extraarticular manifestations of the disease. Osteoarthritis is an articular disease believed to be distinct from rheumatoid arthritis with bone damage being secondary to cartilage degeneration. This degeneration is thought to be either a primary disease of cartilage or a secondary response to stress-induced microfractures of subchondral bone. For both diseases the differential diagnosis is made currently on clinical history and radiological criteria.

In rheumatoid arthritis, immunoglobulin (Ig) complexes are present and resemble classical antigen-induced immune-complexes in their ability to activate the classical complement pathway, stimulate opsonizing activity of macrophages, evoke immediate-type hypersensitivity upon subcutaneous injection, and the like actions. These complexes consist exclusively of immunoglobulins, which implies that immunoglobulin is both the 'antibody' (rheumatoid factor) and the 'antigen'. However, these complexes differ from normal immune-complexes in the low affinity of the binding site (Fab region of rheumatoid factors) for the putative determinant, the preference for homologous association (IgG rheumatoid factors) and, in particular, by the fact that the majority of rheumatoid factors (IgM, IgA, IgG) bind to $\gamma$ class immunoglobulin. It has therefore been argued that there exists in patients with rheumatoid arthritis a structural alteration of $\gamma$ class immunoglobulins (IgG) which creates an antigenically, and presumably immunogenically active sub-population. See Kunkel and Tan, supra. That this antigenic determinant actually exists, and is localised to the $C\gamma2$ domains of altered IgG, has been established by the capacity of rheumatoid factor Fab moieties to bind only to Fc carrying one or both of its $C\gamma2$ domains. This and several other lines of evidence have led to the view that the complexes in rheumatoid arthritis patients involve Fab-Fc (IgG) interactions. It has also been postulated that a large number of immune-complexes in rheumatoid arthritis serum consist predominantly, if not exclusively, of self-associated, altered IgG. That is, those IgG molecules which contain anti-IgG activity in their Fab region also carry the structural abnormality on their Fc region. The view however, that this anti-IgG activity is the result of an evoked auto-antibody to an abnormal IgG sub-population, has been challenged by other investigators who presented data which suggested that the self-association of IgG was not the consequence of true antibody-antigen interactions (not an auto-immune phenomenon).

Efforts to investigate the molecular changes in the Fc region giving rise to these phenomena have largely involved the use of rheumatoid factors as the most specific probes available. However, IgG and IgM rheumatoid factors show two puzzling properties. Firstly, they react to a large extent not only with IgG from the same (diseased) individual, but also with IgG from normal individuals and even other species (e.g., rabbit, rhesus monkey). This implies that the Fc binding site on some of the IgG from patients with rheumatoid arthritis also exists on IgG obtained from patients without disease, but presumably in a latent form. Secondly, in some patients anti-IgG activity is associated with a large proportion (25%) of the total IgG pool, and the resulting complexes constitute over 50%. Thirdly, rheumatoid factor - IgG interactions are invariably monovalent, despite the commonly held view that IgG is a structurally symmetrical molecule and should therefore always possess an even number of determinants. Although steric constraints upon the interaction between rheumatoid factor and target IgG might account for this monovalency, it is possible that glycosylation of IgG in fact renders many molecules structurally asymmetrical (though still actually symmetrical with respect to their polypeptides). If the latter were true, the antigenic determinant on Fc could involve oligosaccharide in some way.

There is no evidence in favour of amino acid changes in the Fc region of IgG from arthritic patients. Several reports however have suggested that total serum IgG or IgG-rheumatoid factor from patients with immune-complex diseases (rheumatoid arthritis, systemic lupus erythematosus) is abnormal with respect to its carbohydrate content. See Pope et al., *J. Immunol.* 115, 365-373 (1975); Hymes et al., *J. Biol. Chem.* 254, 3148-3151 (1979); and Duc Dodon et al., *Immunol.* 42, 401-407 (1981).

It is not apparent from these publications how the immune-complex abnormality can be used, if at all, in diagnostic methodology for rheumatoid arthritis. Commonly used procedures for diagnosis of rheumatoid arthritis are based on serologic reactions. According to these tests, the patient's serum is reacted with a variety of serological systems, all of which contain gamma globulin in some form or a component of Cohn Fraction II obtained from plasma or serum, which is largely gamma globulin. If the patient's serum is positive for the disease, the presence of the so-called rheumatoid factor will cause an agglutination or immunoprecipitation reaction which can be compared with control samples. Such reactions can be determined by various well-known definitive tests which include, for example, electrophoresis, Coombs' (antiglobulin) hemagglutination inhibition test, precipitin reaction, gel diffusion, immunoelectrophoresis, nephelometry, radioimmunoassay and flow cytometry.

A typical component in the agglutination assay for rheumatoid factor involves the use of inert carrier particles such as, for example, latex particles. This assay was first described by Singer and Plotz, *Amer. J. Med.* 21, 888-892 (1956). Modifications of the latex test are described in U.S. Pat. No. 3,088,875 and numerous other patents and publications. Commercial examples of these latex tests for rheumatoid factor are the "Rapi-tex" of Behring Diagnostics, the "RA-TEST" of Hyland Diagnostics and the "RHEUMANOSTICON" of Organon Diagnostics.

Further background information on these conventional diagnostic tests for rheumatoid arthritis can be had by reference to Rose and Friedman, *Manual of Clinical Immunology,* American Society For Microbiology, Washington, D.C., Second Edition, 1980. See, in particular, Horan and Schenk, "Flow Cytometric Analysis of Serum Autoantibodies Applied to the Detection of Rheumatoid Factor," Chapter 9, pp. 56-59; Agnello, "Method for Detection of Immune Complexes Utilizing Clq or Rheumatoid Factors," Chapter 21, pp. 178-185; and Froelich and Williams, "Tests for Detection of Rheumatoid Factors," Chapter 117, pp. 871-873. See also Schur, "Immune-complex assays: The state of the art," *New England Journal of Med.* 298 (3), 161-162 (1978).

Despite the substantial amount of scientific effort in the field, it is apparent that no diagnostic test for rheumatoid arthritis is fully reliable. A significant percentage of classical patients with the disease lack the rheumatoid factor. Accordingly, an improved method for the diagnosis of rheumatoid diseases and related conditions would have substantial use.

BRIEF DESCRIPTION OF THE INVENTION

In accordance with the present invention, a method is provided for the diagnosis of diseases having an arthritic component such as, for example, rheumatoid arthritis and osteoarthritis. The method comprises determining the deficiency of galactose in a sample of the patient's blood serum or plasma, or synovial fluid, or an Ig component or fragment thereof in comparison with the corresponding normal value for galactose.

The deficiency in galactose leads to an increase in the presence of non-reducing terminal N-acetyl-glucoasamine residues. Thus, the invention preferably is carried out by (a) determining the percentage of Ig N-linked oligosaccharide structures carrying an outer arm galactose, or by (b) determining the percentage of non-reducing terminal outer arm N-acetylglucosamine residues. These preferred assays can be performed on whole Ig such as, for example, IgG, or a fragment thereof. Fragments can be, for example, H chain, Fc, or glycopeptides or intact Ig oligosaccharides or oligosaccharide fragments derived from Ig.

Illustrative examples for carrying out the above determination (a) are:

direct enzymatic, or lectin-based assays for galactose such as, for example, (i) direct enzymatic assays for galactose using exo-$\beta$-galactosidases or galactose oxidase, and (ii) direct lectin assays for galactose involving *Ricin communis* agglutinin.

Illustrative examples for carrying out the above determination (b) are:

direct chemical, enzymatic, or lectin-based assays for exposed N-acetyl-glucosamine such as, for example, (i) direct enzymatic assays for $\beta$-N-acetyl-glucosamine involving exo-$\beta$-N-acetyl hexosaminidases, and (ii) direct lectin assays for $\beta$-N-acetyl hexosamine involving wheat germ agglutinin.

The invention also can be carried out by indirect methods such as, for example, determining changes in molecular weight or hydrodynamic volume. That is, the determination can comprise the complete sequencing of all complex oligosaccharides of Ig or any of its above fragments, analysis of the profiles of the asialo or the neutral oligosaccharide fraction of Ig, or changes in the molecular weight of glycopeptides from Ig and its fragments.

In accordance with the invention, it has been found that:

1. The extent of outer-arm galactose $\beta$(1-4) on serum IgG decreases to 50% (p=0.001) in the 'asialo' oligosaccharide fraction of rheumatoid arthritis and 41% (p=0.001) in the neutral oligosaccharide fraction of rheumatoid arthritis. There is a reciprocal increase in the content of non-reducing terminal outer-arm $\beta$(1-2) linked N-acetyl-glucosamine.

2. The extent of outer-arm galactose decreases to 66% (p=0.002) in the asialo population of osteoarthritis and 59% (p=0.002) in the neutral oligosaccharide population of osteoarthritis. There is a reciprocal increase in non-reducing terminal $\beta$(1-2) linked outer-arm N-acetyl-glucosamine.

DETAILED DESCRIPTION OF THE INVENTION

While the specification concludes with claims particularly pointing out and distinctly claiming the subject matter regarded as forming the present invention, it is believed that the invention will be better understood from the following description taken in conjunction with the accompanying drawings in which, briefly:

FIG. 2 shows diagramatically the primary sequences of the N-linked oligosaccharides associated with human IgG. The hydrodynamic volume (as measured in glucose units—g.u.) of each structure (or of its neutral derivative in the case of those sialylated) is indicated. The key to the diagramatic symbols is shown in the lower box. The composite structure also is shown by Rademacher et al., *Biochem. Soc. Trans.* 11, 132-134 (1983).

Figure 3:
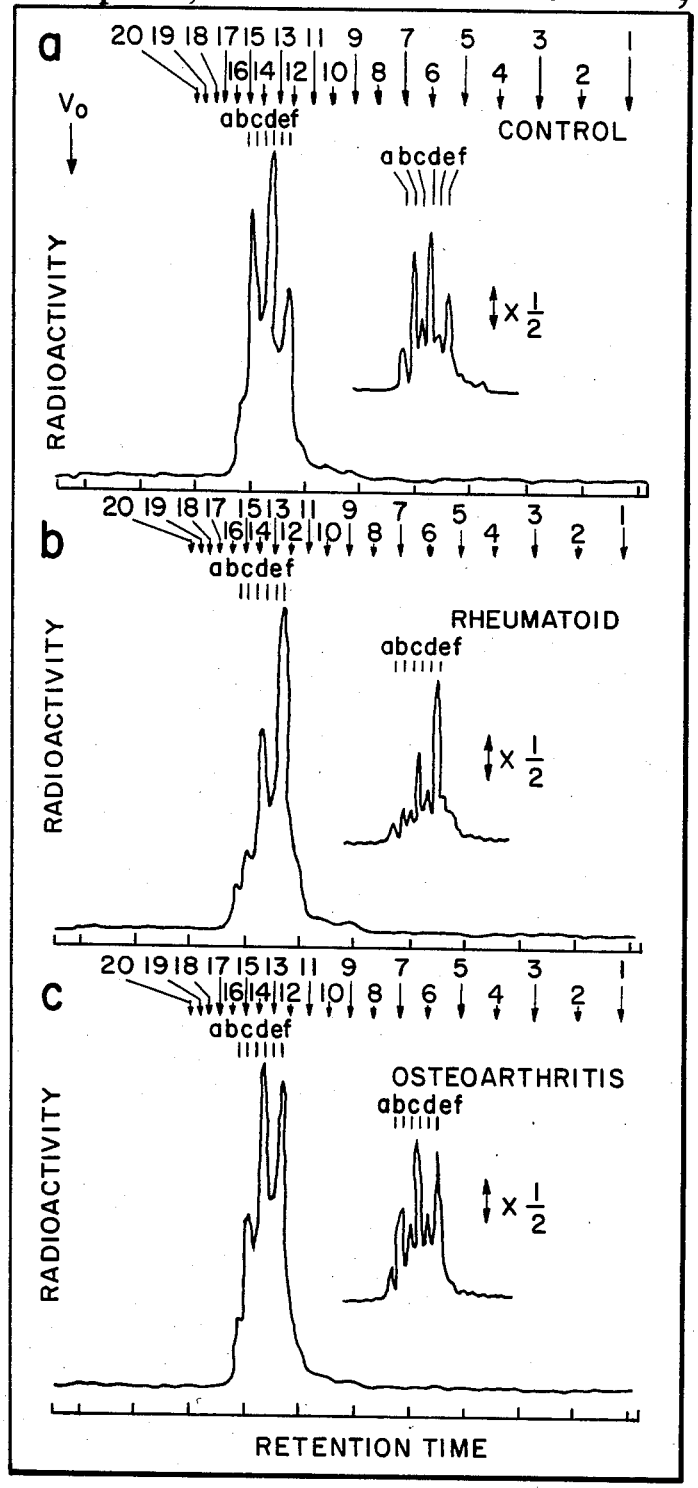

FIG. 3 shows representative Bio-Gel P-4 (−400) gel permeation chromatograms of the asialo oligosaccharides of total serum IgG for (a) control, (b) rheumatoid arthritis and (c) osteoarthritic patients.

Figure 4:
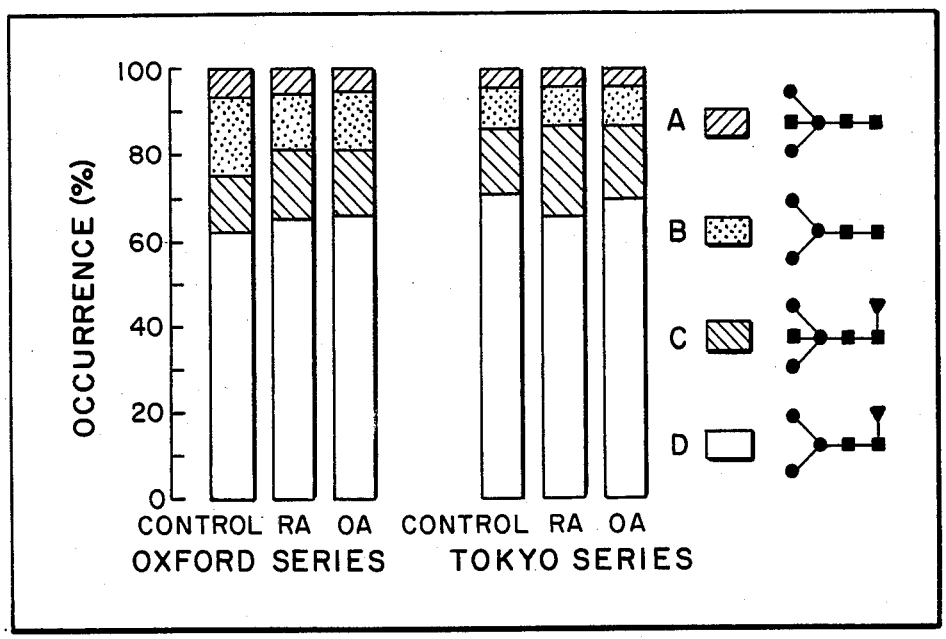

FIG. 4 shows the relative occurrence of the four core structures of the asialo oligosaccharides of total serum IgG for control, rheumatoid arthritis and osteoarthritis patients in two series of studies.

Figure 5:
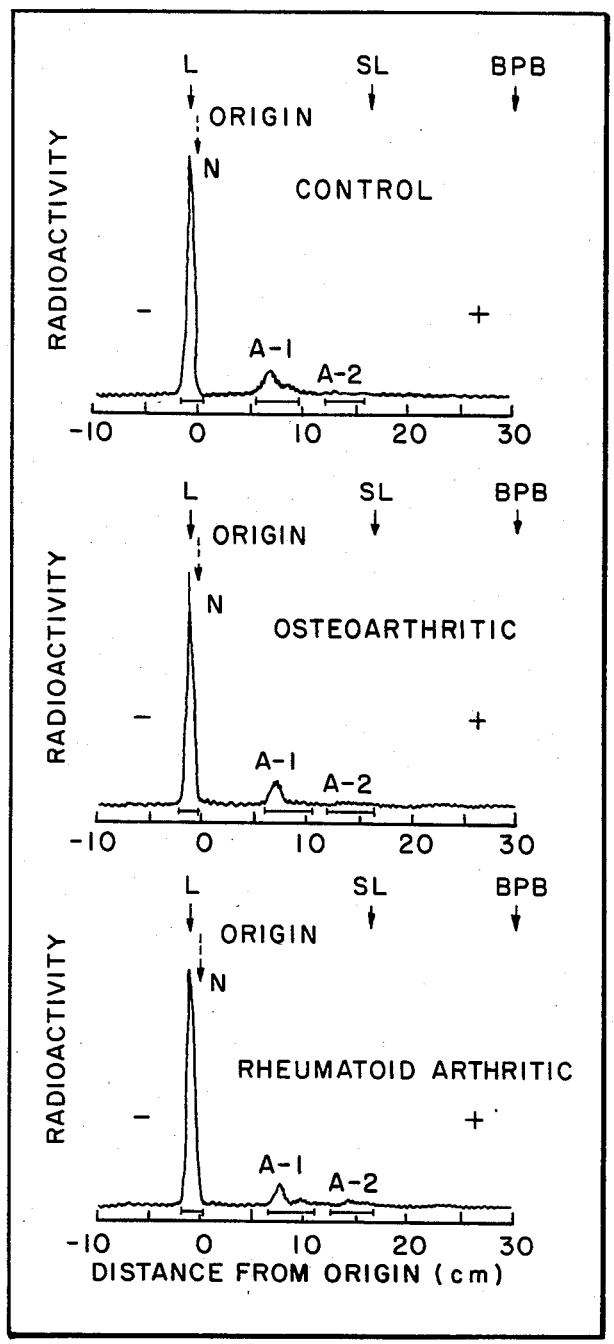

FIG. 5 shows representative radioelectrophoretograms of the oligosaccharides released from the IgG of control, rheumatoid arthritis and osteoarthritis patients.

The following detailed examples will further illustrate the invention although it will be understood that the invention is not limited to these specific illustrative examples.

In these examples, conventional carbohydrate abbreviations and nomenclature are used. Thus, the following symbols are used to indicate nomosaccharide units and their residues in oligosaccharides:

Glucose—Glc
Galactose—Gal
Mannose—Man
Fucose—Fuc

Glyconic acids, glycuronic acids, 2-amino-2-deoxysaccharides, and their N-acetyl derivatives are designated by modified symbols. For example:

N-Acetylglucosamine—GlcNAc
N-Acetylneuraminic acid—NeuNAc

The position and nature of links between units are shown by numerals and the anomeric symbols $\alpha$ and $\beta$. Arrows are used to indicate the direction of the glycoside link with the arrow pointing away from the hemiacetal carbon of the link. For example, a common branched core in oligosaccharides with N-glycosidic protein links can be represented as follows:

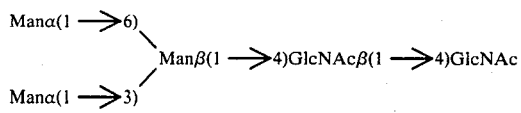

Amino acids also are shown by their conventional symbols. For example:
L-Asparagine—Asn
L-Serine—Ser
L-Threonine—Thr Likewise, antibody structure is designated by conventional nomenclature. The immunoglobulin (Ig) molecules are made up of light (L) and heavy (H) chains. Each of the five classes of Ig molecules has similar sets of light chains, but an antigenically distinctive set of heavy chains named with the corresponding Greek letter ($\gamma$ chains in IgG, $\mu$ in IgM, $\alpha$ in IgA, $\delta$ in IgD, $\epsilon$ in IgE). The amino acid sequence of the N-terminal homology units varies greatly between molecules and is known as the variable (V) region as distinguished from the constant (C) region of the molecules. The N-terminal homology units of light and heavy chains are designated $V_L$ and $V_H$, respectively. Fragments of the antibody molecule obtained by papain digestion are designated the antigen-binding fragments (Fab) and the crystallizable fragment (Fc), while fragments obtained upon pepsin digestion and having small differences are called Fab' (univalent fragment) and F(ab')$_2$ (bivalent fragment).

In order to illustrate the invention, the glycosylation pattern of total IgG isolated from arthritis patients was examined in detail. This was initiated by the inventors in Oxford, U.K. and then performed in collaborative studies conducted simultaneously in Oxford, U.K., and Tokyo, Japan, in which the N-linked oligosaccharides of total serum IgG from various individuals were analysed. In both studies, three groups of individuals were compared - normal controls, osteoarthritic, and rheumatoid arthritic individuals. The results, which required an evaluation of over 1200 primary oligosaccharide sequences from 42 IgG samples, indicate that the rheumatoid arthritis disease state correlates with a marked change in the extent of galactosylation of the oligosaccharide sequences characteristic of human IgG. In addition, total serum IgG from patients with osteoarthritis, show the same type of deficiency at a level intermediate between the normal and rheumatoid states. Importantly, in neither disease does the deficiency lead to novel oligosaccharide structures but rather to an alteration in the relative molar proportions of the normally occurring structures.

EXAMPLE 1

Asparagine-linked Oligosaccharides of IgG

Figure 1A:
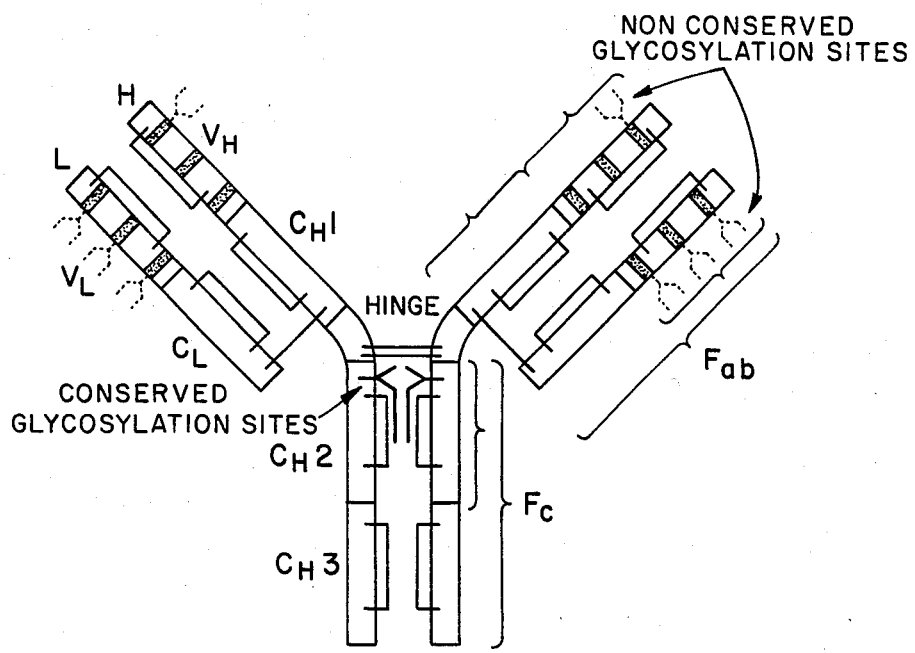
FIG. 1(a) shows the structure of the antibody (IgG) molecule in schematic diagramatic form.

Human serum IgG is a glycoprotein containing on average 2.8 N-linked oligosaccharides per molecule. See Rademacher and Dwek, *Prog. Immunology* 5, 95–112 (1983). These are distributed non-randomly between the two conserved glycosylation sites in the Fc (Asn 297), and the variable glycosylation sites in the Fab region. See Sox and Hood, *Proc. Natl. Acad. Sci. USA* 66, 975–982 (1970) and Spiegelberg et al., *Biochemistry* 9, 217–4223 (1970). The pairing of the oligosaccharides in the interstitial space between the C$\gamma$2 domains often involves oligosaccharides of different primary sequence. See Sutton and Phillips, *Biochem. Soc. Trans.* 11, 130–132 (1983). Consequently, there are discrete subsets of asymmetrical IgG molecules within the-IgG population as a whole. The foregoing is illustrated by FIG. 1(a), as follows:

FIG. 1 (a)

The antibody molecule consists of two heavy (H) and two light (L) chains, linked by disulphide bridges (solid lines) and is divided into homologous regions of sequence ($V_H$, $C_H1$, $C_H2$, $C_H3$), each of which has an intra-chain disulphide bridge. (The pattern of inter-chain disulphide bridging shown here is characteristic of human sub-class IgGb 1). In $V_H$ and $V_L$, the dotted segments represent the hypervariable regions of sequence which, in the three-dimensional structure, together form the antigen binding site. The conserved asparagine-linked biantennary complex oligosaccharide chains are attached to Asn 297 in the $C_H2$ domains. See Sutton and Phillips, supra. Non-conserved oligosaccharide attachment sites are found in the Fab region. Their frequency and location is dependent upon the presence of Asn-X-Ser sites in the hypervariable regions. See Sox and Hood, supra.

Figure 1B:
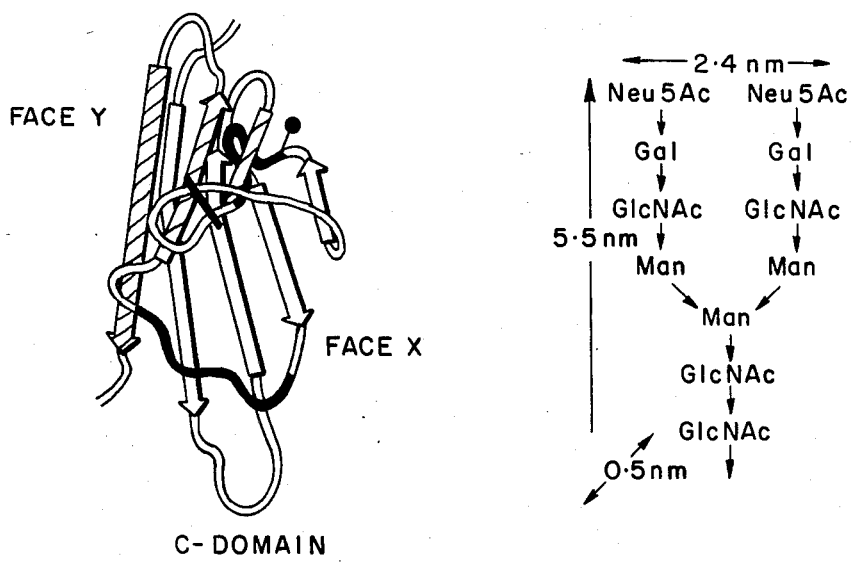
FIG. 1(b) shows the relative size of an immunoglobulin domain and a fully extended N-linked complex oligosaccharide.

The relative sizes of an immunoglobulin domain and a fully extended N-linked complex oligosaccharide are very similar as shown in FIG. 1(b). See also Montreuil, *Biochem. Soc. Trans.* 11, 134–136 (1983). The position of the conserved oligosaccharide on the $C_H2$ domain is indicated in FIG. 1(b). See also Spiegelberg et al., *Biochemistry* 9, 4217–4223 (1970). For the structural and conformational analysis of immunoglobulin-derived N-linked oligosaccharides, see also Rademacher et al., *Biochem Soc. Trans.* 11, 132–134 (1983), and Rademacher and Dwek, *Prog. Immunol.* 5, 95–112 (1983).

At least 30 different complex-type biantennary oligosaccharides have been isolated from human serum IgG. These are illustrated by FIG. 2. In order to compare the molar proportions of each of these structures, each total serum IgG sample was subjected to hydrazinolysis to release intact the oligosaccharide moieties according to the method of Takasaki et al., *Methods in Enzymology* 83, 263–268, Academic Press, 1982. Reduction of the reducing terminal N-acetylglucosamine residues with NaB$^3$H$_4$ was then performed to label radioactively each carbohydrate chain. Each labelled oligosaccharide mixture was then subjected to exhaustive neuraminidase digestion in order to analyse the distribution of neutral structures. These 'asialo' oligosaccharide mixtures were then subjected to Bio-Gel ® P-4 (-400 mesh) gel permeation chromatography, a technique which separates neutral oligosaccharides only on the basis of their effective hydrodynamic volumes as described by Yamashita et al., *Methods in Enzymology* 83, 105–126, Academic Press, 1982. Bio-Gel P-4 is a commercially available porous polyacrylamide bead resin for high resolution gel filtration prepared by copolymerization of acrylamide and N,N'-methylene-bis-acrylamide. See Hjertem and Mosbach, *Anal. Biochem.* 3, 109 (1962). Other suitable gel permeation chromatographic media for separating oligosaccharides by their sizes are, for example, agarose gels and Sephadex ® (cross-linked dextran) gels.

The detailed procedure for carrying out the foregoing hydrazinolysis and gel permeation chromatography was as follows: IgG from the serum of each of 42 individuals was isolated by precipitation at 4° C. with ammonium sulphate (33%) and DE-52 ion-exchange chromatography (4° C.) in 0.01 M $H_2HPO_4$, pH 7.2. DE-52 is a commercially available diethylaminoethyl derivatized ion exchange cellulose in a microgranular form. Each purified IgG (5 mg) was dialysed exhaustively against distilled water (4° C.) and cryogenically dried over activated-charcoal at −196° C. ($<10^{-6}$ torr). Protein samples were suspended in freshly distilled anhydrous hydrazine for 8 hours at 100° C. under an anhydrous argon atmosphere. The hydrazine was removed by repeated (5×) flash-evaporation from anhydrous toluene. The hydrazinolysates were N-acetylated by addition of an excess of acetic anhydride in saturated $NaHCO_3$ at 4° C. After passage through a column of commercially available Dowex® Ag 50×12 (H+form) ion exchange resin to remove $Na^+$, the samples were evaporated to dryness (27° C.), re-dissolved in water, and applied to Whatman 3 MM chromatography paper. Descending paper chromatography (27° C.) was subsequently performed using n-butanol: ethanol:water (4:1:1 v/v) (solvent I). After 48 hours the first 5 cm was eluted with HzO. The oligosaccharides so isolated were flash evaporated to dryness (27° C.) and reduced with a 5 fold excess of $NaB^3H_4$ (7.6 Ci mmole$^{-1}$, New England Nuclear) in 50 mM NaOH, pH 12.0, 30° C. for 4 hours. An equivalent volume of 1 M $NaB^1H_4$ in 50 mM NaOH, pH 12.0, was then added and incubation continued for 2 hours. The mixture was then acidified (pH 5-6) with 1 M acetic acid and passed through a Dowex 50×12 (H+) column, evaporated to dryness (27° C), and flash-evaporated (5×) (27° C. from methanol. The samples were then applied to Whatman 3 MM paper and subjected to descending paper-chromatography for 2 days in solvent I. Radiochromatogram scanning was performed with a Berthold radiochromtogram scanner LB280. The radioactivity at the origin was subsequently eluted with water. An aliquot of reduced [$^3$H]-oligosaccharides so isolated was then subjected to an exhaustive neuraminidase digestion (*Arthobacter ureafaciens*, Nakrai Chemical Co., Kyoto, Japan); radioactive sugar (1×10$^7$ cpm) in 50 μl of 0.1 M sodium acetate pH 5.0, containing 0.1 unit of enzyme. Incubation was performed at 37° C. for 18 hours under a toluene atmosphere. The samples were then subjected to high-voltage paper electrophoresis at 80 V/cm in pyridine/acetic acid/water 3:1:387 v/v, pH 5.4). All radioactivity remained at the origin, thereby confirming the complete cleavage of sialic acid. The samples were recovered from paper by elution with water, desalted using a tandem column of Dowex AG 50×12 (H+) and AG 3×4A (OH−) in water, evaporated to dryness, resuspended in 175 μl of a 20 mg ml$^{-1}$ partial dextran acid hydrolysate and applied to a Bio-Gel P-4 (−400 mesh) gel permeation chromatography column (1.5 cm×200 cm). The column was maintained at 55° C. and water (at 200 μl/min.) was used as the eluent. The eluent was monitored for radioactivity using a Berthold HPLC Radioactivity monitor (model LB503) and for refractive index using a Perkin Elmer Model LC25 refractometer. Analog signals from the monitors were digitized using Nelson analytical ADC interfaces. The digital values were collected and analysed using Hewlett Packard 9836 C computers. FIG. 3 shows radioactivity (vertical axis) plotted against retention time after removal of stochastic noise using Fourier transform techniques. The numerical superscripts above the trace refer to the elution position of glucose oligomers in glucose units (g.u.) as detected simultaneously by the refractive index monitor. Vo is the void position. Sample elution positions (in g.u.) were calculated by cubic spline interpolation between the internal standard glucose oligomer positions. The insets are of resolution-enhanced profiles drawn with the retention time axis unchanged and the radioactivity axis reduced by 0.5. Resolution-enhancement was achieved by lineshape transformation in the Fourier domain.

A comparison of the individual profiles obtained reveals several interesting points.

Firstly, all asialo P-4 chromatograms from control individuals (FIG. 3a) were essentially identical. That is, although any given IgG molecule can contain only a very small number of distinct oligosaccharide structures (i.e. 2 per Fc and additional Fab sugars) the overall relative molar contribution of each of the 30 or so structures in the analysis of polyclonal IgG is remarkably constant. This large number of oligosaccharide sequences is not the result of performing the analysis on polyclonal IgG, since this same 'set' of structures is found on both human myeloma proteins and mouse monoclonal antibodies. Secondly, the asialo P-4 chromatograms from patients with rheumatoid arthritis are essentially the same from one patient to another, but differ significanly and diagnostically from control profiles (FIG. 3b). Thirdly, the asialo oligosaccharide P-4 chromatograms of osteoarthritic patients are also characteristic to all such patients and are distinct from both the control and rheumatoid arthritic profiles (FIG. 3c). Fourthly, and most importantly, the differences between the and most importantly, the differences between the characteristic control and arthritic (osteoarthritic and rheumatoid) asialo P-4 profiles can be rationalised in terms of a population shift towards oligosaccharide structures of lower hydrodynamic volume. To establish the molecular basis of this shift, the asialo oligosaccharides from each patient were analysed with respect to either (1) their relative levels of different core units and (2) the degree and nature of their outer arm substitions.

EXAMPLE 2

Oligosaccharide Cores

In general, complex-type N-linked oligosaccharides can be classified as containing one of four different core structures which are illustrated diagrammatically in FIG. 4. See Mizuochi et al, *J. Immunol.* 129, 2016–2020 (1982). For the biantennary oligosaccharides of IgG, the relative proportions of these four cores can be readily determined by digesting the pool of oligosaccharides with a mixture of *Streptococcus pneumoniae* β-galactosidase and β-N-acetyl-hexosaminidase as described by Mizuochi et al., supra. The resultant digestion products are diagnostic for each of the four cores and differ sufficiently in hydrodynamic volume to be resolved on a P-4 column. The results, summarized in FIG. 4 clearly indicate that there is no systematic correlation between disease state and the incidence of any particular type of core structure.

The detailed procedure for determining the relative occurrence of the four core structures was as follows: An aliquot (3–5×10$^5$ cpm) of the unfractionated asialo oligosaccharides were digested with a mixture of *Strep. pneum.* β-galactosidase (2 milliunits) and β-N-acetyl-hexosaminidase (4 milliunits) in 25 μl of 0.1 M citrate phosphate, pH 6.0. The digestion was performed at 37°

C. for 18 hours under a toluene atmosphere and terminated by heating to 100° C. for 2 mins. After desalting [with Dowex Ag 50×12 (H+), Ag3.4A (OH−)] the digestion products were separated on a Bio-Gel P-4 (−400 mesh) column. Enzymes were purified by a modification of the method of Glasgow et al, *J. Biol. Chem.* 252, 8615-8623 (1977). Strep. pneum. β-galactosidase removes all galactose residues from the asialo oligosaccharides of IgG, irrespective of their core structures. Strep. pneum. β-N-acetyl-hexosaminidase digests the resulting oligosaccharides in a manner dependent on the presence of the (bisecting) GlcNAc β1→4 residue. Specifically, only one N-acetylglucosamine residue (GlcNAc 5 in FIG. 2) is released from the agalactosyl structure GlcNAc β1→2 Man α1→6 (GlcNAc β1→2 Man α1→3) (GlcNAcβ1→4) Man β1→4 GlcNAcβ1→4 (±Fuc α1→6) GlcNAc which is converted to GlcNAcβ1→2 Manα1→6(Man α1→3) (GlcNAc β1→4) Man β1→4 GlcNAc β1→4 (±Fuc α1→6) GlcNAc. However, two N-acetylglucosamine residues are released from GlcNAc β1→2 Man α1→6 (GlcNAcβ1→2 Man α1→3) Man β1→4 GlcNAc β1→4(±Fucα1→6) GlcNAc, which is converted to Man α1→6 (Man α1→3) Man β1→4 GlcNAc β1→4 (±Fuc α1→6) GlcNAc. The four cores have the following structures:

(p=0.001) and 66% (p=0.002),respectively, of the chains contained galactose.

In order to investigate further this galactose deficiency, the ratio in each individual case of digalactosyl to monogalactosyl structures was determined either by chromatography of the galactosylated oligosaccharide chains on *Ricinus communis* agarose, or enzymatically. In the latter, digestion with jack bean β-N-acetyl-hexosaminidase, followed by P-4 gel permeation chromatography, resulted in the resolution of fragments diagnostic of the digalactosylated and monogalactosylated structures. The ratios of the digalactosyl to monogalactosyl structures obtained by both methods were consistent and indicated a decrease of 28% (p<0.02) and 14% (p<0.15) in the rheumatoid and osteoarthritic asialo oligosaccharide mixtures, respectively.

In order to determine if the decreased number of chains containing galactose was secondary to a decrease in outer-arm β(1-2) linked N-acetyl-glucosamine residues, the non-galactosylated structures from each individual were subjected to P-4 chromatography. In all three groups similar profiles where found implying no deficiency in outer-arm β(1-2) linked N-acetyl-glucosamine residues (GlcNAc 5 and 5'). This was subsequently confirmed enzymatically. There can, therefore, be no differences between individuals, irrespective of

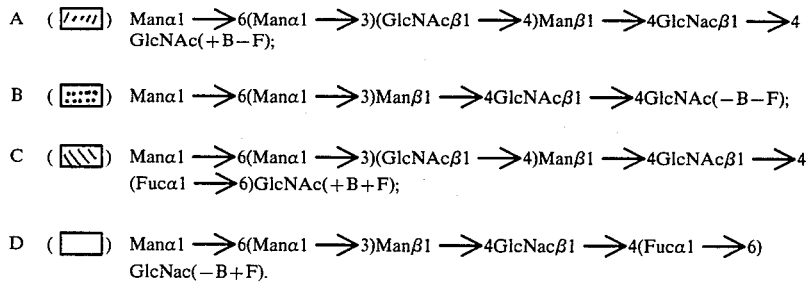

The percentage of each core as determined in the Oxford series were: (+B−F)-control (5.1±3.3), OA (3.5±1.0), RA (4.1±1.4); (−B−F)-control(19.1±6.7), OA (13.5±5.1), RA(16.9±5.9); (+B+F)-control (10.7±6.0), OA (13.0±6.5), RA (10.2±3.1); (−B+F)-control (65.1±1.3), OA (69.7±8.0), RA (70.5±5.8). The values determined in the Tokyo series were: (+B−F-(-control (3.1±0.7), OA (3.7±0.8), RA (4.6±1.4); (−B−F)-control (9.9±3.0), OA (9.7±2.4), RA (8.8±2.1); (+B+F)-control (15.4±0.9), OA (16.6±4.0), RA(20.9±5.7); (−B+F)-control (71.7±2.8), OA(70.1±5.1), RA(65.7±6.7). There is no statistical significance (p>0.05) to the different incidence of any core in the three groups.

In the above ·=bisecting GlcNAc; F=fucose.

EXAMPLE 3

Outer-Arm Substitutions

The outer-arm structures can be characterised with respect to the incidence, linkage and location of galactose, N-acetyl-glucosamine and N-acetyl-neuraminic acid. The asialo oligosaccharide mixtures were therefore first subjected to *Ricinus communis* agarose affinity chromatography to separate galactosylated and non-galactosylated structures. Table 1, below, shows that in control IgG, −75% of all oligosaccharide chains contain at least one galactose residue. In IgG isolated from rheumatoid and osteoarthritic patients only 50% their disease state, with respect to the extent of N-acetyl-glucosaminylation.

Since the negatively charged N-acetyl-neuraminic acid residues confer mobility in an electric field, an aliquot of the labelled oligosaccharide pool (prior to neuraminidase digestion) was subjected to high-voltage paper electrophoresis. The oligosaccharides were completely separated into neutral, monosialylated and disialylated structures (FIG. 5). The occurrence of these is reported in Table 2, below, and the structures present in the three groups are detailed in FIG. 2.

The detailed procedures for obtaining the radioelectrophoretograms of the oligosaccharides released from the IgG of various individuals as illustrated in FIG. 5 was as follows: An aliquot (5×10³ cpm) of [³H]- oligosaccharides was subjected to high-voltage paper electrophoresis (80 V/cm) in pyridine:acetic acid:water (3:1:387 v/v), pH 5.4 (Camag HVE cell 61000). After scanning with a Berthold LB280 Radiochromatogram scanner, the regions N (neutral), A-1 (monosialylated), A-2 (disialylated) were eluted and the dpm in each determined, allowing the ratios in each sample to be calculated. Analog signals from the scanner, were digitized using a Nelson analytical ADC interface and the digital values were collected and analysed using a microcomputer. Lactose (L); (2-3)→sialyllactose (SL); bromophenol blue (BPB).

Within each study, unexpectedly, the two disease states correlate with an identical decrease in the number of chains terminating with one or two N-acetyl-neuraminic acid residues, despite the non-identical changes in the level of galactosylation. The extent of this decrease however, differs between the two studies [36% decrease in Oxf (p=0.001, OA and RA) and 12% decrease in Tok. (p=0.002, OA, p=0.3, RA)].

TABLE 1
Percent oligosaccharide chains lacking galactose in serum IgG*

| Individual Patients | Control | | Osteo-arthritis | | Rheumatoid arthritis | |
|---|---|---|---|---|---|---|
| Oxford Series | Oxf1 | 26.6 | Oxf7 | 38.9 | Oxf13 | 51.5 |
| | Oxf2 | 23.9 | Oxf8 | 36.0 | Oxf14 | 54.7 |
| | Oxf3 | 23.9 | Oxf9 | 26.5 | Oxf15 | 41.9 |
| | Oxf4 | 23.4 | Oxf10 | 35.2 | Oxf16 | 43.6 |
| | Oxf5 | 16.2 | Oxf11 | 31.4 | Oxf17 | 54.9 |
| | Oxf6 | 19.3 | Oxf12 | 33.0 | Oxf18 | 55.0 |
| Tokyo Series | Tok1 | 31.4 | Tok6 | 32.2 | Tok12 | 44.3 |
| | Tok2 | 26.8 | Tok7 | 32.7 | Tok13 | 53.8 |
| | Tok3 | 38.9 | Tok8 | 32.7 | Tok14 | 52.4 |
| | Tok4 | 25.4 | Tok9 | 47.4 | Tok15 | 48.4 |
| | Tok5 | 23.3 | Tok10 | 43.2 | Tok16 | 43.9 |
| | | | Tok11 | 32.4 | Tok17 | 47.9 |
| | | | | | Tok18 | 74.5 |
| | | | | | Tok19 | 56.2 |
| | | | | | Tok20 | 55.6 |
| | | | | | Tok21 | 51.8 |
| | | | | | Tok22 | 44.3 |
| | | | | | Tok23 | 38.7 |
| Arithmetric mean ± s.d. | Oxf 22.9 ± 3.7 | | 33.5 ± 4.3 | | 50.1 ± 5.9 | |
| | Tok 29.2 ± 6.2 | | 36.7 ± 6.1 | | 50.1 ± 9.1 | |
| Pooled Control Serum | Bern-1 24.0 | | | | | |

*Blood samples in the Oxford series were obtained from patients at St. John's Highfield Hospital, Droitwich, U.K. and the Queen Elizabeth Medical Centre, Birmingham, U.K. Patients Oxf13 through Oxf18 and Tok12 through Tok23 fulfilled the American Rheumatism Association criteria for definite or classical rheumatoid arthritis. The Oxf patients range in age from 50-75 yrs. (mean- RA 64 ± 8 SD, OA 68 ± 9 SD). The analysis was performed double-blind with clinical histories obtained after completion of oligosaccharide analysis. In the Oxford Series patients Oxf7, 13 and 14 were Rose-Waaler titer positive. The Rose-Waaler test is a specialized antiglobulin test using sheep erythrocytes sensitized with a subagglutinating dose of rabbit anti-sheep erythrocyte IgG. Rheumatoid factor combines with membrane-bound IgG to produce agglutinatin. See Rose et al., Proc. Soc. Exper. Biol. & Med. 68, 1 (1948). Patients Oxf7 and Oxf8 had long-standing osteoarthritis and very recently have been showing signs of an inflammatory component (6 months and 9 months respectively). Bern-1 refers to IgG from the pooled serum of several thousand individuals and was a kind gift from Dr. U. Nydegger of the Blood Transfusion Center of the Swiss Red Cross, Bern, Switzerland. Non-galactosylated oligosaccharides were isolated as follows. Asialo oligosaccharides $(1 \times 10^7$ cpm) from the IgG of each individual were applied to a Ricin CA-120 agarose column (Miles-Yeda Ltd., Israel, Lot no. AR26) of dimensions 6 mm × 20 cm. The column was developed in 5 mM sodium acetate (pH 5.6). Non-galactosylated structures eluted in the void while digalactosylated and monogalactosylated structures eluted later and at unique volumes. The number of galactoses in each peak was confirmed either by re-passaging the peak on the same Ricin communis agarose column or by following the change in hydrodynamic volume after digestion with jack bean β-N—acetyl hexosaminidase (14 μM substrate, 150 units ml$^{-1}$ of enzyme in 0.1 M citrate phosphate, pH 4.5). The hydrodynamic volume of digalactosylated structures does not change, that of mono-galactosylated ones decrease by 2 g.u. and that of structures lacking galactose by ≧4 g.u. For the Oxford series, the differences in the arithmetic means were significant with p = 0.002 (C vs OA) and p = 0.001 (C vs RA) and p = 0.002 (OA vs RA). For the Tokyo series, the significance was p = 0.05 (C vs OA), p = 0.0007 (C vs RA) and p < 0.0008 (OA vs RA). Any difference in the arithmetic means between the two series was not deemed to be statistically significant. The ratios of digalactosylated to monogalactosylated structures obtained as described above were as follows: C - 0.87 ± 0.10; OA - 0.75 ± 0.14; RA - 0.63 ± 0.12. The statistical significance of these is C vs OA (p = 0.15), C vs RA (p < 0.02, OA vs RA (p = 0.1). Statistical analysis was performed using a non-parametric combined order statistic test (Wilcoxon - Mann - Whitney test as described by Lloyd, "Handbook of Appliation Mathematics," 6 Statistics, Part B, John Wiley and Sons, 1984. Probabilities are quoted for a two-tailed test with a null hypothesis $H_0$: $\mu_1 = \mu_2$ tested against an alternative hypothesis $H_1$: $\mu_1 = \mu_2$.

TABLE 2
Percent oligosaccharide chains containing terminal α(2-6) linked N—acetyl-neuraminic acid*

| | Neutral | Monosialylated | Disialylated |
|---|---|---|---|
| Oxford Series | | | |
| Controls | 75.7 ± 5.0 | 20.5 ± 5.0 | 3.8 ± 1.6 |
| Osteoarthritis | 84.7 ± 1.8 | 13.7 ± 1.5 | 1.7 ± 0.7 |
| Rheumatoid Arthritis | 85.2 ± 1.1 | 12.6 ± 1.2 | 2.2 ± 0.6 |
| Tokyo Series | | | |
| Controls | 75.6 ± 0.8 | 17.8 ± 2.1 | 6.6 ± 1.6 |
| Osteoarthritis | 78.6 ± 2.1 | 16.5 ± 1.8 | 5.0 ± 0.9 |
| Rheumatoid Arthritis | 78.4 ± 4.4 | 15.2 ± 3.2 | 6.5 ± 1.5 |

*See description of FIG 5, above. In order to confirm that all structures present in the A-1 and A-2 positions of FIG. 5 contained only one and two sialic acid residues, respectively, an aliquot of the eluted A-1 and A-2 oligosaccharide fractions was applied to a QAE - A25 Sephadex ® column (6 mm × 10 cm). Samples were applied in 2 mM ammonium acetate (pH 5.3) and the column developed with a 2 mM to 350 mM linear gradient of ammonium acetate. Both the A-1 and A-2 fractions from the paper electophoresis gave single elution peaks corresponding to the standard elutions positions of monosialylated and disialylated oligosaccharides respectively. QAE - A25 Sephadex is a cross-linked dextran ion exchange resin with the functional group diethyl-(2-hydroxypropyl)aminoethyl.

The results above show that osteoarthritis and particularly rheumatoid arthritis are associated with marked changes in the level of outer-arm galactosylation of the complex N-linked oligosaccharides of total serum IgG. The absolute degree of galactosylation was found to be disease specific. The observed changes in galactosylation correlate highly with both disease states (p=0.002 OA vs C, p=0.001 RA vs C) and between disease states (p=0.002 OA vs RA). Importantly, no novel primary oligosaccharide sequences were found to be associated with IgG from either arthritide. More significant then the loss of galactose (−33% in rheumatoid arthritis) is the increased exposure at the non-reducing terminus of N-acetylglucosamine (−100%). Given the phenomenon of oligosaccharide pairing in Fc and its restrictions, simple calculations reveal that there would be a consequent and marked elevation in the incidence of Fc molecules which totally lack galactose (−300% in rheumatoid arthritis and −60% in osteoarthris). Thus the hierarchical set of changes, beginning with an altered level of galactosylation and proceeding via a change in the relative populations of a constant set of oligosaccharides structures, leads, through the phenomenon of pairing, to dramatic changes in the incidence of individual Fc sub-populations.

Various other examples will be apparent to the person skilled in the art after reading the present disclosure without departing from the spirit and scope of the invention and it is intended that all such further examples be included within the scope of the appended claims.

What is claimed is:

1. A method for the diagnosis of rheumatoid arthritis or osteoarthritis as a sole syndrome or as a component of other rheumatic diseases comprising determining the deficiency of outer-arm galactosylation of an IgG component or fragment thereof in a patient's blood serum or plasma or synovial fluid by assaying for the incidence of non-reducing terminal outer arm N-acetylglucosamine residues of said IgG component or fragment and comparing with corresponding normal control values.

* * * * *

UNITED STATES PATENT AND TRADEMARK OFFICE
CERTIFICATE OF CORRECTION

PATENT NO. : 4,659,659

DATED : April 21, 1987

INVENTOR(S) : RAYMOND A. DWEK and THOMAS W. RADEMACHER

It is certified that error appears in the above—identified patent and that said Letters Patent is hereby corrected as shown below:

In col. 5, line 68, the page number "217" should read --4217--.

In col. 7, line 24, the formula "$H_zO$" should read --$H_2O$--.

In col. 9, line 55, after "In the above" insert --B--.

In col. 10, line 58, the number "$10^3$" should read --$10^6$--.

Signed and Sealed this

First Day of September, 1987

*Attest:*

DONALD J. QUIGG

*Attesting Officer*  *Commissioner of Patents and Trademarks*